US010015987B2

(12) United States Patent
Henry, Jr. et al.

(10) Patent No.: US 10,015,987 B2
(45) Date of Patent: Jul. 10, 2018

(54) TRIGGER-BASED WIRELESS BROADCASTING FOR AEROSOL DELIVERY DEVICES

(71) Applicant: R. J. REYNOLDS TOBACCO COMPANY, Winston-Salem, NC (US)

(72) Inventors: Raymond Charles Henry, Jr., Cary, NC (US); Glen Joseph Kimsey, Cary, NC (US); Frederic Philippe Ampolini, Winston-Salem, NC (US)

(73) Assignee: RAI STRATEGIC HOLDINGS INC., Winston-Salem, NC (US)

( * ) Notice: Subject to any disclaimer, the term of this patent is extended or adjusted under 35 U.S.C. 154(b) by 368 days.

(21) Appl. No.: 14/808,233

(22) Filed: Jul. 24, 2015

(65) Prior Publication Data

US 2017/0023952 A1 Jan. 26, 2017

(51) Int. Cl.
*A24F 47/00* (2006.01)
*H04W 4/80* (2018.01)
(Continued)

(52) U.S. Cl.
CPC .......... *A24F 47/008* (2013.01); *A61M 15/06* (2013.01); *G05B 15/02* (2013.01); *G05D 7/0676* (2013.01); *H04W 4/80* (2018.02)

(58) Field of Classification Search
CPC ........ G05B 15/02; H04W 4/008; H04W 4/80; A61M 15/06;
(Continued)

(56) References Cited

U.S. PATENT DOCUMENTS 1,771,366 A 7/1930 Wyss et al.
2,057,353 A 10/1936 Whittemore, Jr.
(Continued)

FOREIGN PATENT DOCUMENTS

AU 276250 7/1965
CA 2 641 869 5/2010
(Continued)

OTHER PUBLICATIONS

Cavoukian, A., "Fact Sheet: Wireless Communication Technologies: Safeguarding Privacy and Security", Office of the Information and Privacy Commision/Ontario [online], 2007 [retrieved Jan. 3, 2018], Retrieved from Internet: <URL: http://rnao.ca/sites/rnao-ca/files/IPC_Fact_Sheet_14_Safeguards_for_Wireless_Technologies_0.pdf>, pp. 1-4.*
(Continued)

*Primary Examiner* — Todd Aguilera
(74) *Attorney, Agent, or Firm* — Womble Bond Dickinson (US) LLP (57) ABSTRACT

An aerosol delivery device comprising a control component and a communication interface is provided. The control component controls operation of at least one functional element of the aerosol delivery device in instances in which a flow of air through at least a portion of the at least one housing is detected. The communication interface is coupled to the control component and enables wireless communication. The control component further detects a predefined trigger, and automatically in response thereto, causes the communication interface to broadcast availability of the aerosol delivery device for connection with a capable wireless device. The predefined trigger includes at least one instance in which the flow of air is detected, and excludes user-actuation of any button on the aerosol delivery device.

18 Claims, 4 Drawing Sheets

(51) Int. Cl.
*A61M 15/06* (2006.01)
*G05D 7/06* (2006.01)
*G05B 15/02* (2006.01)

(58) Field of Classification Search
CPC .............. A61M 2016/0015–2016/0039; A24F 47/002–47/008; G05D 7/06; G05D 7/0676
USPC ......... 700/275, 282–283; 392/386, 387, 394, 392/397–398, 404; 131/194, 273, 131/328–330; 128/200.14, 202.21, 128/203.12, 203.26, 203.27, 204.17
See application file for complete search history.

(56) References Cited

U.S. PATENT DOCUMENTS

| | | |
|---|---|---|
| 2,104,266 A | 1/1938 | McCormick |
| 3,200,819 A | 8/1965 | Gilbert |
| 4,284,089 A | 8/1981 | Ray |
| 4,303,083 A | 12/1981 | Burruss, Jr. |
| 4,735,217 A | 4/1988 | Gerth et al. |
| 4,848,374 A | 7/1989 | Chard et al. |
| 4,907,606 A | 3/1990 | Lilja et al. |
| 4,922,901 A | 5/1990 | Brooks et al. |
| 4,945,931 A | 8/1990 | Gori |
| 4,947,874 A | 8/1990 | Brooks et al. |
| 4,947,875 A | 8/1990 | Brooks et al. |
| 4,986,286 A | 1/1991 | Roberts et al. |
| 5,019,122 A | 5/1991 | Clearman et al. |
| 5,042,510 A | 8/1991 | Curtiss et al. |
| 5,060,671 A | 10/1991 | Counts et al. |
| 5,093,894 A | 3/1992 | Deevi et al. |
| 5,144,962 A | 9/1992 | Counts et al. |
| 5,249,586 A | 10/1993 | Morgan et al. |
| 5,261,424 A | 11/1993 | Sprinkel, Jr. |
| 5,322,075 A | 6/1994 | Deevi et al. |
| 5,353,813 A | 10/1994 | Deevi et al. |
| 5,369,723 A | 11/1994 | Counts et al. |
| 5,372,148 A | 12/1994 | McCafferty et al. |
| 5,388,574 A | 2/1995 | Ingebrethsen et al. |
| 5,408,574 A | 4/1995 | Deevi et al. |
| 5,468,936 A | 11/1995 | Deevi et al. |
| 5,498,850 A | 3/1996 | Das |
| 5,515,842 A | 5/1996 | Ramseyer et al. |
| 5,530,225 A | 6/1996 | Hajaligol |
| 5,564,442 A | 10/1996 | MacDonald et al. |
| 5,649,554 A | 7/1997 | Sprinkel et al. |
| 5,666,977 A | 9/1997 | Higgins et al. |
| 5,687,746 A | 11/1997 | Rose et al. |
| 5,692,492 A * | 12/1997 | Bruna ................ A61M 15/009 128/200.14 |
| 5,726,421 A | 3/1998 | Fleischhauer et al. |
| 5,727,571 A | 3/1998 | Meiring et al. |
| 5,743,251 A | 4/1998 | Howell et al. |
| 5,799,663 A | 9/1998 | Gross et al. |
| 5,819,756 A | 10/1998 | Mielordt |
| 5,865,185 A | 2/1999 | Collins et al. |
| 5,865,186 A | 2/1999 | Volsey, II |
| 5,878,752 A | 3/1999 | Adams et al. |
| 5,894,841 A | 4/1999 | Voges |
| 5,934,289 A | 8/1999 | Watkins et al. |
| 5,954,979 A | 9/1999 | Counts et al. |
| 5,967,148 A | 10/1999 | Harris et al. |
| 6,040,560 A | 3/2000 | Fleischhauer et al. |
| 6,053,176 A | 4/2000 | Adams et al. |
| 6,089,857 A | 7/2000 | Matsuura et al. |
| 6,095,153 A | 8/2000 | Kessler et al. |
| 6,125,853 A | 10/2000 | Susa et al. |
| 6,155,268 A | 12/2000 | Takeuchi |
| 6,164,287 A | 12/2000 | White |
| 6,196,218 B1 | 3/2001 | Voges |
| 6,196,219 B1 | 3/2001 | Hess et al. |
| 6,598,607 B2 | 7/2003 | Adiga et al. |
| 6,601,776 B1 | 8/2003 | Oljaca et al. |
| 6,615,840 B1 | 9/2003 | Fournier et al. |
| 6,688,313 B2 | 2/2004 | Wrenn et al. |
| 6,772,756 B2 | 8/2004 | Shayan |
| 6,803,545 B2 | 10/2004 | Blake et al. |
| 6,854,461 B2 | 2/2005 | Nichols |
| 6,854,470 B1 | 2/2005 | Pu |
| 7,117,867 B2 | 10/2006 | Cox et al. |
| 7,293,565 B2 | 11/2007 | Griffin et al. |
| 7,513,253 B2 | 4/2009 | Kobayashi et al. |
| 7,775,459 B2 | 8/2010 | Martens, III et al. |
| 7,832,410 B2 | 11/2010 | Hon |
| 7,845,359 B2 | 12/2010 | Montaser |
| 7,896,006 B2 | 3/2011 | Hamano et al. |
| 8,127,772 B2 | 3/2012 | Montaser |
| 8,314,591 B2 | 11/2012 | Terry et al. |
| 8,365,742 B2 | 2/2013 | Hon |
| 8,402,976 B2 | 3/2013 | Fernando et al. |
| 8,499,766 B1 | 8/2013 | Newton |
| 8,528,569 B1 | 9/2013 | Newton |
| 8,550,069 B2 | 10/2013 | Alelov |
| 8,851,081 B2 | 10/2014 | Fernando et al. |
| 9,414,217 B2 * | 8/2016 | Knaappila .............. H04W 8/005 |
| 9,614,815 B2 * | 4/2017 | Grange ............... H04L 63/0428 |
| 2002/0146242 A1 | 10/2002 | Vieira |
| 2003/0226837 A1 | 12/2003 | Blake et al. |
| 2004/0118401 A1 | 6/2004 | Smith et al. |
| 2004/0129280 A1 | 7/2004 | Woodson et al. |
| 2004/0200488 A1 | 10/2004 | Felter et al. |
| 2004/0226568 A1 | 11/2004 | Takeuchi et al. |
| 2005/0016550 A1 | 1/2005 | Katase |
| 2006/0016453 A1 | 1/2006 | Kim |
| 2006/0196518 A1 | 9/2006 | Hon |
| 2007/0074734 A1 | 4/2007 | Braunshteyn et al. |
| 2007/0102013 A1 | 5/2007 | Adams et al. |
| 2007/0215167 A1 | 9/2007 | Crooks et al. |
| 2008/0085103 A1 | 4/2008 | Beland et al. |
| 2008/0092912 A1 | 4/2008 | Robinson et al. |
| 2008/0257367 A1 | 10/2008 | Paterno et al. |
| 2008/0276947 A1 | 11/2008 | Martzel |
| 2008/0302374 A1 | 12/2008 | Wengert et al. |
| 2009/0095287 A1 | 4/2009 | Emarlou |
| 2009/0095311 A1 | 4/2009 | Hon |
| 2009/0095312 A1 | 4/2009 | Herbrich et al. |
| 2009/0126745 A1 | 5/2009 | Hon |
| 2009/0188490 A1 | 7/2009 | Hon |
| 2009/0230117 A1 | 9/2009 | Fernando et al. |
| 2009/0272379 A1 | 11/2009 | Thorens et al. |
| 2009/0283103 A1 | 11/2009 | Nielsen et al. |
| 2009/0320863 A1 | 12/2009 | Fernando et al. |
| 2010/0043809 A1 | 2/2010 | Magnon |
| 2010/0083959 A1 | 4/2010 | Siller |
| 2010/0200006 A1 | 8/2010 | Robinson et al. |
| 2010/0229881 A1 | 9/2010 | Hearn |
| 2010/0242974 A1 | 9/2010 | Pan |
| 2010/0307518 A1 | 12/2010 | Wang |
| 2010/0313901 A1 | 12/2010 | Fernando et al. |
| 2011/0005535 A1 | 1/2011 | Xiu |
| 2011/0011396 A1 | 1/2011 | Fang |
| 2011/0036363 A1 | 2/2011 | Urtsev et al. |
| 2011/0036365 A1 | 2/2011 | Chong et al. |
| 2011/0094523 A1 | 4/2011 | Thorens et al. |
| 2011/0126848 A1 | 6/2011 | Zuber et al. |
| 2011/0155153 A1 | 6/2011 | Thorens et al. |
| 2011/0155718 A1 | 6/2011 | Greim et al. |
| 2011/0168194 A1 | 7/2011 | Hon |
| 2011/0265806 A1 | 11/2011 | Alarcon et al. |
| 2011/0309157 A1 | 12/2011 | Yang et al. |
| 2012/0042885 A1 | 2/2012 | Stone et al. |
| 2012/0060853 A1 | 3/2012 | Robinson et al. |
| 2012/0111347 A1 | 5/2012 | Hon |
| 2012/0132643 A1 | 5/2012 | Choi et al. |
| 2012/0227752 A1 | 9/2012 | Alelov |
| 2012/0231464 A1 | 9/2012 | Yu et al. |
| 2012/0260927 A1 | 10/2012 | Liu |
| 2012/0279512 A1 | 11/2012 | Hon |
| 2012/0318882 A1 | 12/2012 | Abehasera |
| 2013/0037041 A1 | 2/2013 | Worm et al. |
| 2013/0056013 A1 | 3/2013 | Terry et al. |
| 2013/0081625 A1 | 4/2013 | Rustad et al. |

(56) References Cited

U.S. PATENT DOCUMENTS

| | | |
|---|---|---|
| 2013/0081642 A1 | 4/2013 | Safari |
| 2013/0192619 A1 | 8/2013 | Tucker et al. |
| 2013/0255702 A1 | 10/2013 | Griffith, Jr. et al. |
| 2013/0284192 A1* | 10/2013 | Peleg .................. A24F 47/002 131/329 |
| 2013/0306084 A1 | 11/2013 | Flick |
| 2013/0319439 A1 | 12/2013 | Gorelick et al. |
| 2013/0319440 A1* | 12/2013 | Capuano ............. A24F 47/008 131/329 |
| 2013/0340750 A1 | 12/2013 | Thorens et al. |
| 2013/0340775 A1 | 12/2013 | Juster et al. |
| 2014/0000638 A1 | 1/2014 | Sebastian et al. |
| 2014/0060554 A1 | 3/2014 | Collett et al. |
| 2014/0060555 A1 | 3/2014 | Chang et al. |
| 2014/0096781 A1 | 4/2014 | Sears et al. |
| 2014/0096782 A1 | 4/2014 | Ampolini et al. |
| 2014/0109921 A1 | 4/2014 | Chen |
| 2014/0157583 A1 | 6/2014 | Ward et al. |
| 2014/0209105 A1 | 7/2014 | Sears et al. |
| 2014/0253144 A1 | 9/2014 | Novak et al. |
| 2014/0261408 A1 | 9/2014 | DePiano et al. |
| 2014/0261486 A1 | 9/2014 | Potter et al. |
| 2014/0261487 A1 | 9/2014 | Chapman et al. |
| 2014/0261495 A1 | 9/2014 | Novak et al. |
| 2014/0270727 A1 | 9/2014 | Ampolini et al. |
| 2014/0270729 A1 | 9/2014 | DePiano et al. |
| 2014/0270730 A1 | 9/2014 | DePiano et al. |
| 2014/0345631 A1 | 11/2014 | Bowen et al. |
| 2015/0007838 A1 | 1/2015 | Fernando et al. |
| 2015/0053217 A1 | 2/2015 | Steingraber et al. |
| 2015/0188891 A1* | 7/2015 | Grange ............... H04L 63/0428 380/270 |
| 2015/0319600 A1* | 11/2015 | Knaappila ............. H04W 8/005 455/41.2 |
| 2017/0079329 A1* | 3/2017 | Zitzke .................. A24F 47/008 |

FOREIGN PATENT DOCUMENTS

| | | |
|---|---|---|
| CN | 1541577 | 11/2004 |
| CN | 2719043 | 8/2005 |
| CN | 200997909 | 1/2008 |
| CN | 101116542 | 2/2008 |
| CN | 101176805 | 5/2008 |
| CN | 201379072 | 1/2010 |
| DE | 10 2006 004 484 | 8/2007 |
| DE | 102006041042 | 3/2008 |
| DE | 20 2009 010 400 | 11/2009 |
| EP | 0 295 122 | 12/1988 |
| EP | 0 430 566 | 6/1991 |
| EP | 0 845 220 | 6/1998 |
| EP | 1 618 803 | 1/2006 |
| EP | 2 316 286 | 5/2011 |
| GB | 2469850 | 11/2010 |
| WO | WO 1997/48293 | 12/1997 |
| WO | WO 2003/034847 | 5/2003 |
| WO | WO 2004/043175 | 5/2004 |
| WO | WO 2004/080216 | 9/2004 |
| WO | WO 2005/099494 | 10/2005 |
| WO | WO 2007/078273 | 7/2007 |
| WO | WO 2007/131449 | 11/2007 |
| WO | WO 2009/105919 | 9/2009 |
| WO | WO 2009/155734 | 12/2009 |
| WO | WO 2010/003480 | 1/2010 |
| WO | WO 2010/045670 | 4/2010 |
| WO | WO 2010/073122 | 7/2010 |
| WO | WO 2010/118644 | 10/2010 |
| WO | WO 2010/140937 | 12/2010 |
| WO | WO 2011/010334 | 1/2011 |
| WO | WO 2012/072762 | 6/2012 |
| WO | WO 2012/100523 | 8/2012 |
| WO | WO 2013/089551 | 6/2013 |
| WO | 2016120124 A1 | 8/2015 |
| WO | 2016007352 A1 | 1/2016 |
| WO | 2016141147 A1 | 9/2016 |

OTHER PUBLICATIONS

International Search Report for International Application No. PCT/US2016/043131 dated Oct. 31, 2016.

* cited by examiner

TRIGGER-BASED WIRELESS BROADCASTING FOR AEROSOL DELIVERY DEVICES

TECHNOLOGICAL FIELD

The present disclosure relates to aerosol delivery devices such as smoking articles that may utilize electrically generated heat for the production of aerosol (e.g., smoking articles commonly referred to as electronic cigarettes), and more particularly to aerosol delivery devices that initiate wireless broadcasting for connection with capable wireless devices based on the detection of triggers. The smoking articles may be configured to heat an aerosol precursor, which may incorporate materials that may be made or derived from, or otherwise incorporate tobacco, the precursor being capable of forming an inhalable substance for human consumption.

BACKGROUND

Many smoking devices have been proposed through the years as improvements upon, or alternatives to, smoking products that require combusting tobacco for use. Many of those devices purportedly have been designed to provide the sensations associated with cigarette, cigar or pipe smoking, but without delivering considerable quantities of incomplete combustion and pyrolysis products that result from the burning of tobacco. To this end, there have been proposed numerous smoking products, flavor generators and medicinal inhalers that utilize electrical energy to vaporize or heat a volatile material, or attempt to provide the sensations of cigarette, cigar or pipe smoking without burning tobacco to a significant degree. See, for example, the various alternative smoking articles, aerosol delivery devices and heat generating sources set forth in the background art described in U.S. Pat. No. 7,726,320 to Robinson et al., U.S. Pat. App. Pub. No. 2013/0255702 to Griffith Jr. et al., and U.S. Pat. App. Pub. No. 2014/0096781 to Sears et al., all of which are incorporated herein by reference in their entireties. See also, for example, the various types of smoking articles, aerosol delivery devices and electrically-powered heat generating sources referenced by brand name and commercial source in U.S. patent application Ser. No. 14/170,838 to Bless et al., filed Feb. 3, 2014, which is incorporated herein by reference in its entirety. Additionally, other types of smoking articles have been proposed in U.S. Pat. No. 5,505,214 to Collins et al., U.S. Pat. No. 5,894,841 to Voges, U.S. Pat. No. 6,772,756 to Shayan, U.S. Pat. App. Pub. No. 2006/0196518 to Hon, and U.S. Pat. App. Pub. No. 2007/0267031 to Hon, all of which are incorporated herein by reference in their entireties.

Ongoing developments in the field of aerosol delivery devices have resulted in increasingly sophisticated aerosol delivery devices. For example, some aerosol delivery devices are enabled to wirelessly communicate (e.g., Bluetooth® communication) with other capable wireless devices. This communication generally requires an initial setup process in which the aerosol delivery device broadcast advertisements for connecting with capable wireless devices, and in response thereto, further establishes a line of communication with at least one device. However, initiation of this process may be complex due to the lack of user input buttons, at the aerosol delivery device, for use in initiating broadcasting. Therefore, a need exist for a wireless broadcasting method that is initiated independent of user-actuation of any button on the aerosol delivery device.

BRIEF SUMMARY

The present disclosure relates to aerosol delivery devices, methods of forming such devices, and elements of such devices. The present disclosure thus includes, without limitation, the following example implementations. In some example implementations, an aerosol delivery device is provided that includes at least one housing, and a control component and communication interface, contained with the at least one housing. The control component is configured to control operation of at least one functional element of the aerosol delivery device in instances in which a flow of air through at least a portion of the at least one housing is detected. The communication interface is coupled to the control component and configured to enable wireless communication in which the control component is further configured to detect a predefined trigger, and automatically in response thereto, cause the communication interface to broadcast availability of the aerosol delivery device for connection with a capable wireless device. The predefined trigger includes at least one instance in which the flow of air is detected, and excludes user-actuation of any button on the aerosol delivery device.

In some example implementations of the aerosol delivery device of the preceding or any subsequent example implementation, or any combination thereof, the trigger includes a predefined length of time between at least two instances in which the flow of air is detected.

In some example implementations of the aerosol delivery device of any preceding or any subsequent example implementation, or any combination thereof, the predefined length of time is no more than approximately 1,250 milliseconds between the at least two instances in which the flow of air is detected.

In some example implementations of the aerosol delivery device of any preceding or any subsequent example implementation, or any combination thereof, the trigger includes a predefined duration of an instance in which the flow of air is detected.

In some example implementations of the aerosol delivery device of any preceding or any subsequent example implementation, or any combination thereof, the predefined duration is between approximately 70 and 750 milliseconds.

In some example implementations of the aerosol delivery device of any preceding or any subsequent example implementation, or any combination thereof, the trigger includes a predefined number of instances in which the flow of air is detected.

In some example implementations of the aerosol delivery device of any preceding or any subsequent example implementation, or any combination thereof, the aerosol delivery device comprises a control body including the at least one housing, control component and communication interface. The control body is coupleable to a charging component and a cartridge, and the trigger further includes coupling of the control body to the charging component or cartridge.

In some example implementations of the aerosol delivery device of any preceding or any subsequent example implementation, or any combination thereof, the trigger further includes coupling of the control body to the cartridge, and the at least one instance is the first instance in which the flow of air is detected after the coupling of the control body to the cartridge.

In some example implementations of the aerosol delivery device of any preceding or any subsequent example implementation, or any combination thereof, the communication interface is a Bluetooth communication interface, and the communication interface being caused to broadcast availability includes the Bluetooth communication interface being caused to transmit an advertisement that includes information for connecting the Bluetooth communication interface with a capable Bluetooth-enabled device, and in at least one instance, bond with the capable Bluetooth-enabled device upon connection.

In some example implementations of the aerosol delivery device of any preceding or any subsequent example implementation, or any combination thereof, the aerosol delivery device comprises a control body including the at least one housing, control component and Bluetooth communication interface, and the trigger further includes coupling of the control body to a cartridge, and the at least one instance is the first instance in which the flow of air is detected after the coupling of the control body to the cartridge, and the Bluetooth communication interface being caused to transmit the advertisement includes being caused to transmit the advertisement for a length of time no longer than a predetermined length of time after the first instance, and thereafter cease transmission of the advertisement.

In some example implementations, a method is provided for operation of an aerosol delivery device. The method comprises, at the aerosol delivery device, a control component controlling operation of at least one functional element of the aerosol delivery device in instances in which a flow of air through at least a portion of the at least one housing is detected. The method also comprises a communication interface enabling wireless communication; and the control component further detecting a predefined trigger, and automatically in response thereto, causing the communication interface to broadcast availability of the aerosol delivery device for connection with a capable wireless device, the predefined trigger including at least one instance in which the flow of air is detected, and excluding user-actuation of any button on the aerosol delivery device.

In some example implementations of the method of the preceding or any subsequent example implementation, or any combination thereof, the trigger includes a predefined length of time between at least two instances in which the flow of air is detected.

In some example implementations of the method of any preceding or any subsequent example implementation, or any combination thereof, the predefined length of time is no more than approximately 1,250 milliseconds between the at least two instances in which the flow of air is detected.

In some example implementations of the method of any preceding or any subsequent example implementation, or any combination thereof, the trigger includes a predefined duration of an instance in which the flow of air is detected.

In some example implementations of the method of any preceding or any subsequent example implementation, or any combination thereof, the predefined duration is between approximately 70 and 750 milliseconds.

In some example implementations of the method of any preceding or any subsequent example implementation, or any combination thereof, the trigger includes a predefined number of instances in which the flow of air is detected.

In some example implementations of the method of any preceding or any subsequent example implementation, or any combination thereof, the aerosol delivery device comprises a control body coupleable to a charging component and a cartridge, and the trigger further includes coupling of the control body to the charging component or cartridge.

In some example implementations of the method of any preceding or any subsequent example implementation, or any combination thereof, the trigger further includes coupling of the control body to the cartridge, and the at least one instance is the first instance in which the flow of air is detected after the coupling of the control body to the cartridge.

In some example implementations of the method of any preceding or any subsequent example implementation, or any combination thereof, the communication interface is a Bluetooth communication interface, and the communication interface broadcasting availability includes the Bluetooth communication interface transmitting an advertisement that includes information for connecting the Bluetooth communication interface with a capable Bluetooth-enabled device, and in at least one instance, bonding with the capable Bluetooth-enabled device upon connection.

In some example implementations of the method of any preceding or any subsequent example implementation, or any combination thereof, the aerosol delivery device comprises a control body including the control component and Bluetooth communication interface, and the trigger further includes coupling of the control body to a cartridge, and the at least one instance is the first instance in which the flow of air is detected after the coupling of the control body to the cartridge, and the Bluetooth communication interface transmitting the advertisement includes transmitting the advertisement for a length of time no longer than a predetermined length of time after the first instance, and thereafter cease transmission of the advertisement.

These and other features, aspects, and advantages of the present disclosure will be apparent from a reading of the following detailed description together with the accompanying drawings, which are briefly described below. The present disclosure includes any combination of two, three, four or more features or elements set forth in this disclosure, regardless of whether such features or elements are expressly combined or otherwise recited in a specific example implementation described herein. This disclosure is intended to be read holistically such that any separable features or elements of the disclosure, in any of its aspects and example implementations, should be viewed as intended, namely to be combinable, unless the context of the disclosure clearly dictates otherwise.

It will therefore be appreciated that this Brief Summary is provided merely for purposes of summarizing some example implementations so as to provide a basic understanding of some aspects of the disclosure. Accordingly, it will be appreciated that the above described example implementations are merely examples and should not be construed to narrow the scope or spirit of the disclosure in any way. Other example implementations, aspects and advantages will become apparent from the following detailed description taken in conjunction with the accompanying drawings which illustrate, by way of example, the principles of some described example implementations.

BRIEF DESCRIPTION OF THE DRAWING(S)

Having thus described the disclosure in the foregoing general terms, reference will now be made to the accompanying drawings, which are not necessarily drawn to scale, and wherein:

FIG. 2 is a partially cut-away view of an aerosol delivery device that according to various example implementations may correspond to the aerosol delivery device of FIG. 1;

FIG. 3 is a state diagram for trigger-based Bluetooth advertising, according to example implementations; and FIG. 4 illustrates various operations in a method of operation of an aerosol delivery device, according to an example implementation of the present disclosure.

DETAILED DESCRIPTION

The present disclosure will now be described more fully hereinafter with reference to example implementations thereof. These example implementations are described so that this disclosure will be thorough and complete, and will fully convey the scope of the disclosure to those skilled in the art. Indeed, the disclosure may be embodied in many different forms and should not be construed as limited to the implementations set forth herein; rather, these implementations are provided so that this disclosure will satisfy applicable legal requirements. As used in the specification and the appended claims, the singular forms "a," "an," "the" and the like include plural referents unless the context clearly dictates otherwise.

As described hereinafter, example implementations of the present disclosure relate to aerosol delivery systems. Aerosol delivery systems according to the present disclosure use electrical energy to heat a material (preferably without combusting the material to any significant degree) to form an inhalable substance; and components of such systems have the form of articles most preferably are sufficiently compact to be considered hand-held devices. That is, use of components of preferred aerosol delivery systems does not result in the production of smoke in the sense that aerosol results principally from by-products of combustion or pyrolysis of tobacco, but rather, use of those preferred systems results in the production of vapors resulting from volatilization or vaporization of certain components incorporated therein. In some example implementations, components of aerosol delivery systems may be characterized as electronic cigarettes, and those electronic cigarettes most preferably incorporate tobacco and/or components derived from tobacco, and hence deliver tobacco derived components in aerosol form.

Aerosol generating pieces of certain preferred aerosol delivery systems may provide many of the sensations (e.g., inhalation and exhalation rituals, types of tastes or flavors, organoleptic effects, physical feel, use rituals, visual cues such as those provided by visible aerosol, and the like) of smoking a cigarette, cigar or pipe that is employed by lighting and burning tobacco (and hence inhaling tobacco smoke), without any substantial degree of combustion of any component thereof. For example, the user of an aerosol generating piece of the present disclosure can hold and use that piece much like a smoker employs a traditional type of smoking article, draw on one end of that piece for inhalation of aerosol produced by that piece, take or draw puffs at selected intervals of time, and the like.

Aerosol delivery systems of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like.

Aerosol delivery systems of the present disclosure generally include a number of components provided within an outer body or shell, which may be referred to as a housing. The overall design of the outer body or shell can vary, and the format or configuration of the outer body that can define the overall size and shape of the aerosol delivery device can vary. Typically, an elongated body resembling the shape of a cigarette or cigar can be a formed from a single, unitary housing or the elongated housing can be formed of two or more separable bodies. For example, an aerosol delivery device can comprise an elongated shell or body that can be substantially tubular in shape and, as such, resemble the shape of a conventional cigarette or cigar. In one example, all of the components of the aerosol delivery device are contained within one housing. Alternatively, an aerosol delivery device can comprise two or more housings that are joined and are separable. For example, an aerosol delivery device can possess at one end a control body comprising a housing containing one or more reusable components (e.g., a rechargeable battery and various electronics for controlling the operation of that article), and at the other end and integral with or removably coupled thereto, an outer body or shell containing a disposable portion (e.g., a disposable flavor-containing cartridge).

Aerosol delivery systems of the present disclosure most preferably comprise some combination of a power source (i.e., an electrical power source), at least one control component (e.g., means for actuating, controlling, regulating and ceasing power for heat generation, such as by controlling electrical current flow the power source to other components of the article—e.g., a microprocessor, individually or as part of a microcontroller), a heater or heat generation member (e.g., an electrical resistance heating element or other component, which alone or in combination with one or more further elements may be commonly referred to as an "atomizer"), an aerosol precursor composition (e.g., commonly a liquid capable of yielding an aerosol upon application of sufficient heat, such as ingredients commonly referred to as "smoke juice," "e-liquid" and "e-juice"), and a mouth end region or tip for allowing draw upon the aerosol delivery device for aerosol inhalation (e.g., a defined airflow path through the article such that aerosol generated can be withdrawn therefrom upon draw).

More specific formats, configurations and arrangements of components within the aerosol delivery systems of the present disclosure will be evident in light of the further disclosure provided hereinafter. Additionally, the selection and arrangement of various aerosol delivery system components can be appreciated upon consideration of the commercially available electronic aerosol delivery devices, such as those representative products referenced in background art section of the present disclosure.

In various examples, an aerosol delivery device can comprise a reservoir configured to retain the aerosol precursor composition. The reservoir particularly can be formed of a porous material (e.g., a fibrous material) and thus may be referred to as a porous substrate (e.g., a fibrous substrate).

A fibrous substrate useful as a reservoir in an aerosol delivery device can be a woven or nonwoven material formed of a plurality of fibers or filaments and can be formed of one or both of natural fibers and synthetic fibers. For example, a fibrous substrate may comprise a fiberglass material. In particular examples, a cellulose acetate material can be used. In other example implementations, a carbon material can be used. A reservoir may be substantially in the form of a container and may include a fibrous material included therein.

FIG. 1 illustrates a side view of an aerosol delivery device 100 including a control body 102 and a cartridge 104, according to various example implementations of the present disclosure. In particular, FIG. 1 illustrates the control body and the cartridge coupled to one another. The control body and the cartridge may be permanently or detachably aligned in a functioning relationship. Various mechanisms may connect the cartridge to the control body to result in a threaded engagement, a press-fit engagement, an interference fit, a magnetic engagement or the like. The aerosol delivery device may be substantially rod-like, substantially tubular shaped, or substantially cylindrically shaped in some example implementations when the cartridge and the control body are in an assembled configuration. The cartridge and control body may include a unitary housing or outer body or separate, respective housings or outer bodies, which may be formed of any of a number of different materials. The housing may be formed of any suitable, structurally-sound material. In some examples, the housing may be formed of a metal or alloy, such as stainless steel, aluminum or the like. Other suitable materials include various plastics (e.g., polycarbonate), metal-plating over plastic and the like.

In some example implementations, one or both of the control body 102 or the cartridge 104 of the aerosol delivery device 100 may be referred to as being disposable or as being reusable. For example, the control body may have a replaceable battery or a rechargeable battery and thus may be combined with any type of recharging technology, including connection to a typical alternating current electrical outlet, connection to a car charger (i.e., a cigarette lighter receptacle), and connection to a computer, such as through a universal serial bus (USB) cable or connector. Further, in some example implementations, the cartridge may comprise a single-use cartridge, as disclosed in U.S. Pat. No. 8,910,639 to Chang et al., which is incorporated herein by reference in its entirety.

In one example implementation, the control body 102 and cartridge 104 forming the aerosol delivery device 100 may be permanently coupled to one another. Examples of aerosol delivery devices that may be configured to be disposable and/or which may include first and second outer bodies that are configured for permanent coupling are disclosed in U.S. patent application Ser. No. 14/170,838 to Bless et al., filed Feb. 3, 2014, which is incorporated herein by reference in its entirety. In another example implementation, the cartridge and control body may be configured in a single-piece, non-detachable form and may incorporate the components, aspects, and features disclosed herein. However, in another example implementation, the control body and cartridge may be configured to be separable such that, for example, the cartridge may be refilled or replaced.

FIG. 2 illustrates a more particular example implementation of the aerosol delivery device 100. As seen in the cut-away view illustrated therein, the aerosol delivery device can comprise a control body 102 and cartridge 104. As illustrated in FIG. 2, the control body can be formed of a control body shell 206 that can include a control component 208 (e.g., a microprocessor, individually or as part of a microcontroller), a flow sensor 210, a battery 212, and one or more light-emitting diodes (LEDs) 214, and such components may be variably aligned. Further indicators (e.g., a haptic feedback component, an audio feedback component, or the like) can be included in addition to or as an alternative to the LED. The cartridge can be formed of a cartridge shell 216 enclosing a reservoir 218 that is in fluid communication with a liquid transport element 220 adapted to wick or otherwise transport an aerosol precursor composition stored in the reservoir housing to a heater 222 (sometimes referred to as a heating element). In some example, a valve may be positioned between the reservoir and heater, and configured to control an amount of aerosol precursor composition passed or delivered from the reservoir to the heater.

Various examples of materials configured to produce heat when electrical current is applied therethrough may be employed to form the heater 222. The heater in these examples may be resistive heating element such as a wire coil. Example materials from which the wire coil may be formed include Kanthal (FeCrAl), Nichrome, Molybdenum disilicide ($MoSi_2$), molybdenum silicide (MoSi), Molybdenum disilicide doped with Aluminum ($Mo(Si,Al)_2$), graphite and graphite-based materials (e.g., carbon-based foams and yarns) and ceramics (e.g., positive or negative temperature coefficient ceramics). Example implementations of heaters or heating members useful in aerosol delivery devices according to the present disclosure are further described below, and can be incorporated into devices such as illustrated in FIG. 2 as described herein.

An opening 224 may be present in the cartridge shell 216 (e.g., at the mouthend) to allow for egress of formed aerosol from the cartridge 104. Such components are representative of the components that may be present in a cartridge and are not intended to limit the scope of cartridge components that are encompassed by the present disclosure.

The cartridge 104 also may include one or more electronic components 226, which may include an integrated circuit, a memory component, a sensor, or the like. The electronic components may be adapted to communicate with the control component 208 and/or with an external device by wired or wireless means. The electronic components may be positioned anywhere within the cartridge or a base 228 thereof.

Although the control component 208 and the flow sensor 210 are illustrated separately, it is understood that the control component and the flow sensor may be combined as an electronic circuit board with the air flow sensor attached directly thereto. Further, the electronic circuit board may be positioned horizontally relative to the illustration of FIG. 1 in that the electronic circuit board can be lengthwise parallel to the central axis of the control body. In some examples, the air flow sensor may comprise its own circuit board or other base element to which it can be attached. In some examples, a flexible circuit board may be utilized. A flexible circuit board may be configured into a variety of shapes, include substantially tubular shapes. In some examples, a flexible circuit board may be combined with, layered onto, or form part or all of a heater substrate as further described below.

The control body 102 and the cartridge 104 may include components adapted to facilitate a fluid engagement therebetween. As illustrated in FIG. 2, the control body can include a coupler 230 having a cavity 232 therein. The base 228 of the cartridge can be adapted to engage the coupler and can include a projection 234 adapted to fit within the cavity. Such engagement can facilitate a stable connection between the control body and the cartridge as well as establish an electrical connection between the battery 212 and control component 208 in the control body and the heater 222 in the cartridge. Further, the control body shell 206 can include an air intake 236, which may be a notch in the shell where it connects to the coupler that allows for passage of ambient air around the coupler and into the shell where it then passes through the cavity 232 of the coupler and into the cartridge through the projection 234.

Figure 2:
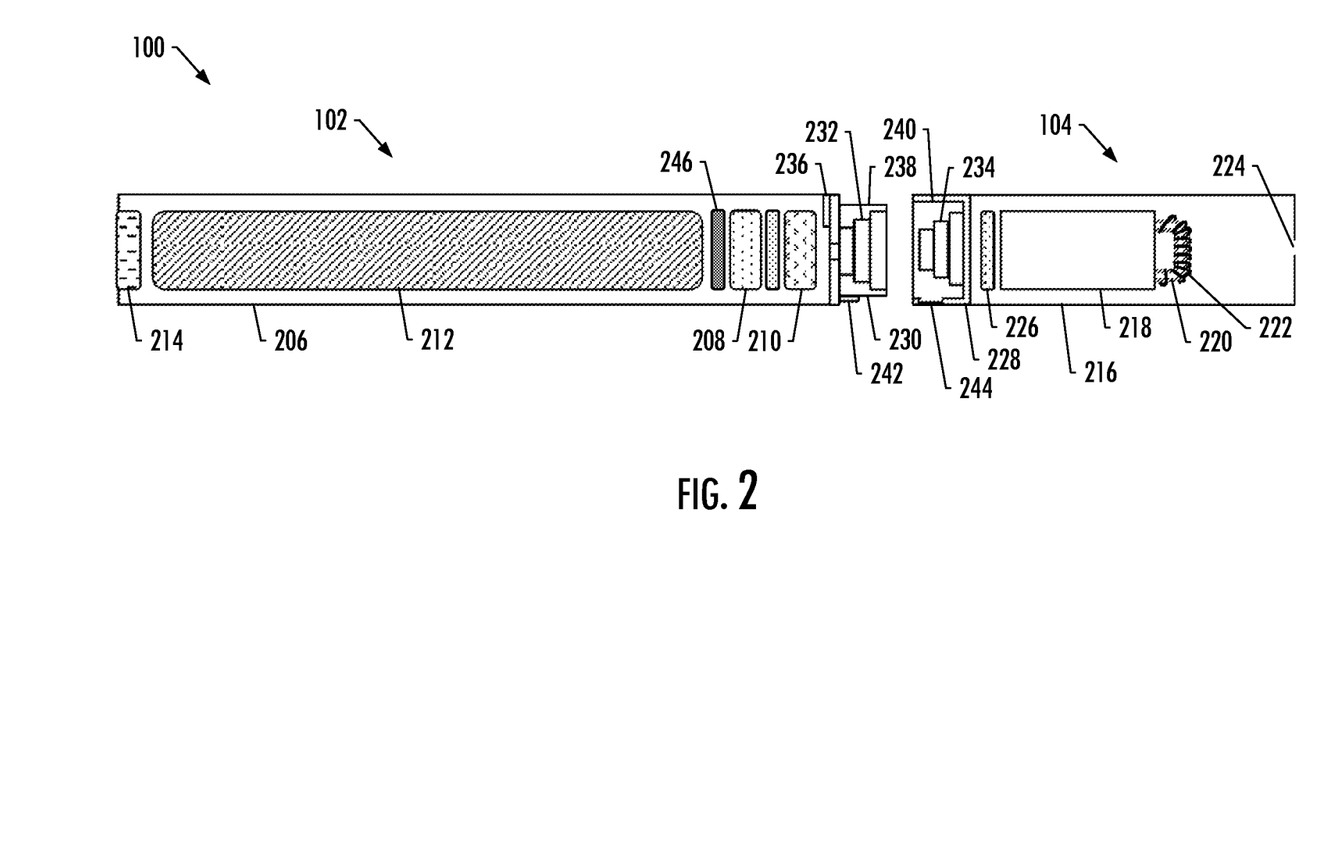

A coupler and a base useful according to the present disclosure are described in U.S. Pat. App. Pub. No. 2014/0261495 to Novak et al., which is incorporated herein by reference in its entirety. For example, the coupler 230 as seen in FIG. 2 may define an outer periphery 238 configured to mate with an inner periphery 240 of the base 228. In one example the inner periphery of the base may define a radius that is substantially equal to, or slightly greater than, a radius of the outer periphery of the coupler. Further, the coupler may define one or more protrusions 242 at the outer periphery configured to engage one or more recesses 244 defined at the inner periphery of the base. However, various other examples of structures, shapes and components may be employed to couple the base to the coupler. In some examples the connection between the base of the cartridge 104 and the coupler of the control body 102 may be substantially permanent, whereas in other examples the connection therebetween may be releasable such that, for example, the control body may be reused with one or more additional cartridges that may be disposable and/or refillable.

The aerosol delivery device 100 may be substantially rod-like or substantially tubular shaped or substantially cylindrically shaped in some examples. In other examples, further shapes and dimensions are encompassed—e.g., a rectangular or triangular cross-section, multifaceted shapes, or the like.

The reservoir 218 illustrated in FIG. 2 can be a container or can be a fibrous reservoir, as presently described. For example, the reservoir can comprise one or more layers of nonwoven fibers substantially formed into the shape of a tube encircling the interior of the cartridge shell 216, in this example. An aerosol precursor composition can be retained in the reservoir. Liquid components, for example, can be sorptively retained by the reservoir. The reservoir can be in fluid connection with the liquid transport element 220. The liquid transport element can transport the aerosol precursor composition stored in the reservoir via capillary action to the heater 222 that is in the form of a metal wire coil in this example. As such, the heater is in a heating arrangement with the liquid transport element. Example implementations of reservoirs and transport elements useful in aerosol delivery devices according to the present disclosure are further described below, and such reservoirs and/or transport elements can be incorporated into devices such as illustrated in FIG. 2 as described herein. In particular, specific combinations of heating members and transport elements as further described below may be incorporated into devices such as illustrated in FIG. 2 as described herein.

In use, when a user draws on the aerosol delivery device 100, airflow is detected by the flow sensor 210, and the heater 222 is activated to vaporize components of the aerosol precursor composition. Drawing upon the mouthend of the aerosol delivery device causes ambient air to enter the air intake 236 and pass through the cavity 232 in the coupler 230 and the central opening in the projection 234 of the base 228. In the cartridge 104, the drawn air combines with the formed vapor to form an aerosol. The aerosol is whisked, aspirated or otherwise drawn away from the heater and out the opening 224 in the mouthend of the aerosol delivery device.

In some examples, the aerosol delivery device 100 may include a number of additional software-controlled functions. For example, the aerosol delivery device may include a battery protection circuit configured to detect battery input, loads on the battery terminals, and charging input. The battery protection circuit may include short-circuit protection and under-voltage lock out. The aerosol delivery device may also include components for ambient temperature measurement, and its control component 208 may be configured to control at least one functional element to inhibit battery charging if the ambient temperature is below a certain temperature (e.g., 0° C.) or above a certain temperature (e.g., 45° C.) prior to start of charging or during charging.

Power delivery from the battery 212 may vary over the course of each puff on the device 100 according to a power control mechanism. The device may include a "long puff" safety timer such that in the event that a user or an inadvertent mechanism causes the device to attempt to puff continuously, the control component 208 may control at least one functional element to terminate the puff automatically after some period of time (e.g., four seconds). Further, the time between puffs on the device may be restricted to less than a period of time (e.g., 100). A watchdog safety timer may automatically reset the aerosol delivery device if its control component or software running on it becomes unstable and does not service the timer within an appropriate time interval (e.g., eight seconds). Further safety protection may be provided in the event of a defective or otherwise failed flow sensor 210, such as by permanently disabling the aerosol delivery device in order to prevent inadvertent heating. A puffing limit switch may deactivate the device in the event of a pressure sensor fail causing the device to continuously activate without stopping after the four second maximum puff time.

The aerosol delivery device 100 may include a puff tracking algorithm configured for heater lockout once a defined number of puffs has been achieved for an attached cartridge (based on the number of available puffs calculated in light of the e-liquid charge in the cartridge). In some implementations, the puff tracking algorithm indirectly counts the number of puffs based on a corresponding number of puff seconds. As such, the puff tracking algorithm may incrementally count a number of puff seconds in order to calculate when a specified number of puffs have occurred and subsequently shut off the device once the puff seconds reach what is estimated to be a pre-determined number of puffs. For example, if three (3) seconds is defined to be equivalent to one "average" puff and the device have been configured to shut down after two hundred (200) average puffs, the device may shut down after six hundred (600) puff second have elapsed with respect to usage of the cartridge. The puff tracking algorithm may further estimate the amount of e-liquid that is utilized per puff second, and mathematically calculate the e-liquid volume based at least in part on the estimation of corresponding puffs seconds.

The various components of an aerosol delivery device according to the present disclosure can be chosen from components described in the art and commercially available. Examples of batteries that can be used according to the disclosure are described in U.S. Pat. App. Pub. No. 2010/0028766 to Peckerar et al., which is incorporated herein by reference in its entirety.

The aerosol delivery device 100 can incorporate the sensor 210 or another sensor or detector for control of supply of electric power to the heater 222 when aerosol generation is desired (e.g., upon draw during use). As such, for example, there is provided a manner or method of turning off the power supply to the heater when the aerosol delivery device is not be drawn upon during use, and for turning on the power supply to actuate or trigger the generation of heat by the heater during draw. Additional representative types of sensing or detection mechanisms, structure and configuration thereof, components thereof, and general methods of operation thereof, are described in U.S. Pat. No. 5,261,424 to Sprinkel, Jr., U.S. Pat. No. 5,372,148 to McCafferty et al., and PCT Pat. App. Pub. No. WO 2010/003480 to Flick, all of which are incorporated herein by reference in their entireties.

The aerosol delivery device 100 most preferably incorporates the control component 208 or another control mechanism for controlling the amount of electric power to the heater 222 during draw. Representative types of electronic components, structure and configuration thereof, features thereof, and general methods of operation thereof, are described in U.S. Pat. No. 4,735,217 to Gerth et al., U.S. Pat. No. 4,947,874 to Brooks et al., U.S. Pat. No. 5,372,148 to McCafferty et al., U.S. Pat. No. 6,040,560 to Fleischhauer et al., U.S. Pat. No. 7,040,314 to Nguyen et al., U.S. Pat. No. 8,205,622 to Pan, U.S. Pat. App. Pub. No. 2009/0230117 to Fernando et al., U.S. Pat. App. Pub. No. 2014/0060554 to Collet et al., U.S. Pat. App. Pub. No. 2014/0270727 to Ampolini et al., and U.S. patent application Ser. No. 14/209,191 to Henry et al., filed Mar. 13, 2014, all of which are incorporated herein by reference in their entireties.

Representative types of substrates, reservoirs or other components for supporting the aerosol precursor are described in U.S. Pat. No. 8,528,569 to Newton, U.S. Pat. App. Pub. No. 2014/0261487 to Chapman et al., U.S. patent application Ser. No. 14/011,992 to Davis et al., filed Aug. 28, 2013, and U.S. patent application Ser. No. 14/170,838 to Bless et al., filed Feb. 3, 2014, all of which are incorporated herein by reference in their entireties. Additionally, various wicking materials, and the configuration and operation of those wicking materials within certain types of electronic cigarettes, are set forth in U.S. Pat. App. Pub. No. 2014/0209105 to Sears et al., which is incorporated herein by reference in its entirety.

The aerosol precursor composition, also referred to as a vapor precursor composition, may comprise a variety of components including, by way of example, a polyhydric alcohol (e.g., glycerin, propylene glycol or a mixture thereof), nicotine, tobacco, tobacco extract and/or flavorants. Various components that may be included in the aerosol precursor composition are described in U.S. Pat. No. 7,726,320 to Robinson et al., which is incorporated herein by reference in its entirety. Additional representative types of aerosol precursor compositions are set forth in U.S. Pat. No. 4,793,365 to Sensabaugh, Jr. et al., U.S. Pat. No. 5,101,839 to Jakob et al., U.S. Pat. No. 6,779,531 to Biggs et al., U.S. Pat. App. Pub. No. 2013/0008457 to Zheng et al., and *Chemical and Biological Studies on New Cigarette Prototypes that Heat Instead of Burn Tobacco*, R. J. Reynolds Tobacco Company Monograph (1988), all of which are incorporated herein by reference in their entireties.

Additional representative types of components that yield visual cues or indicators may be employed in the aerosol delivery device 100, such as LEDs and related components, auditory elements (e.g., speakers), vibratory elements (e.g., vibration motors) and the like. Examples of suitable LED components, and the configurations and uses thereof, are described in U.S. Pat. No. 5,154,192 to Sprinkel et al., U.S. Pat. No. 8,499,766 to Newton, U.S. Pat. No. 8,539,959 to Scatterday, and U.S. patent application Ser. No. 14/173,266 to Sears et al., filed Feb. 5, 2014, all of which are incorporated herein by reference in their entireties.

Yet other features, controls or components that can be incorporated into aerosol delivery devices of the present disclosure are described in U.S. Pat. No. 5,967,148 to Harris et al., U.S. Pat. No. 5,934,289 to Watkins et al., U.S. Pat. No. 5,954,979 to Counts et al., U.S. Pat. No. 6,040,560 to Fleischhauer et al., U.S. Pat. No. 8,365,742 to Hon, U.S. Pat. No. 8,402,976 to Fernando et al., U.S. Pat. App. Pub. No. 2005/0016550 to Katase, U.S. Pat. App. Pub. No. 2010/0163063 to Fernando et al., U.S. Pat. App. Pub. No. 2013/0192623 to Tucker et al., U.S. Pat. App. Pub. No. 2013/0298905 to Leven et al., U.S. Pat. App. Pub. No. 2013/0180553 to Kim et al., U.S. Pat. App. Pub. No. 2014/0000638 to Sebastian et al., U.S. Pat. App. Pub. No. 2014/0261495 to Novak et al., and U.S. Pat. App. Pub. No. 2014/0261408 to DePiano et al., all of which are incorporated herein by reference in their entireties.

The control component 208 includes a number of electronic components, and in some examples may be formed of a printed circuit board (PCB) that supports and electrically connects the electronic components. Examples of suitable electronic components include a microprocessor or processor core, an integrated circuit, a memory, and the like. In some examples, the control component may include a microcontroller with an integrated processor core and memory, and which may further include one or more integrated input/output peripherals.

The aerosol delivery device 100 may further include a communication interface 246 coupled to the control component 208, and which may be configured to enable wireless communication. In some examples, the communication interface may be included on the PCB of the control component, or a separate PCB that may be coupled to the PCB or one or more components of the control component. The communication interface may enable the aerosol delivery device to wirelessly communicate with one or more networks, computing devices or other appropriately-enabled devices. Examples of suitable computing devices include any of a number of different mobile computers. More particular examples of suitable mobile computers include portable computers (e.g., laptops, notebooks, tablet computers), mobile phones (e.g., cell phones, smartphones), wearable computers (e.g., smartwatches) and the like. In other examples, the computing device may be embodied as other than a mobile computer, such as in the manner of a desktop computer, server computer or the like. And in yet another example, the computing device may be embodied as an electric beacon such as one employing iBeacon™ technology developed by Apple Inc. Examples of suitable manners according to which the aerosol delivery device may be configured to wirelessly communicate are disclosed in U.S. patent application Ser. No. 14/327,776, filed Jul. 10, 2014, to Ampolini et al., and U.S. patent application Ser. No. 14/609,032, filed Jan. 29, 2015, to Henry, Jr. et al., each of which is incorporated herein by reference in its entirety.

The communication interface 246 may include, for example, an antenna (or multiple antennas) and supporting hardware and/or software for enabling wireless communication with a communication network (e.g., a cellular network, Wi-Fi, WLAN, and/or the like), and/or for supporting device-to-device, short-range communication, in accordance with one or more desired communication technologies. The communication interface may at times be composed of multiple separate or integrated communication interfaces enabling communication in accordance with multiple communication technologies. Examples of suitable short-range communication technologies that may be supported by the communication interface include various near field communication (NFC) technologies, wireless personal area network (WPAN) technologies and the like. More particular examples of suitable WPAN technologies include those specified by IEEE 802.15 standards or otherwise, including Bluetooth®, Bluetooth low energy (Bluetooth LE), Zigbee®, infrared (e.g., IrDA), radio-frequency identification (RFID), Wireless USB and the like. Yet other examples of suitable short-range communication technologies include Wi-Fi Direct, as well as certain other technologies based on or specified by IEEE 802.11 standards and that support direct device-to-device communication.

In some example implementations, the aerosol delivery device 100 may utilize trigger-based wireless broadcasting as a means for initializing connection to other capable wireless devices (e.g., mobile computers), which connection to and communication with these devices may be enabled by the communication interface 246. In this regard, the control component 208 may detect a predefined trigger, and automatically in response thereto, cause the communication interface to broadcast availability of the aerosol delivery device for connection with a capable wireless device. As used herein, the broadcasting availability of the aerosol delivery device for connection with a capable wireless device may be simply referred to as "broadcasting availability."

In some examples, the predefined trigger may include at least one instance in which the flow of air is detected, and exclude user-actuation of any button on the aerosol delivery device 100. The trigger may be defined such that the range of difficulty in implementing and/or performing the trigger varies from to easy to moderately difficult. In an instance in which the trigger is moderately difficult for a user of the aerosol delivery device to perform, inadvertent occurrences of broadcasting availability may be prevented.

In some example implementations, the trigger includes a predefined number of instances in which the flow of air is detected. In some implementations, the trigger includes a predefined length of time between at least two instances in which the flow of air is detected. In one implementation, for example, the predefined length of time is no more than approximately 1,250 milliseconds between at least two instances in which the flow of air is detected. In other implementations, however, the predefined length of time may be greater than approximately 1,250 milliseconds between at least two instances in which the flow of air is detected.

In some implementations, the trigger includes a predefined duration of an instance in which the flow of air is detected. In one implementation, for example, the predefined duration is between approximately 70 and 750 milliseconds. In other implementations, however, the predefined duration may be less than approximately 70 milliseconds or greater than approximately 750 milliseconds between at least two instances in which the flow of air is detected.

It should be noted that the trigger may include any one, or multiple combinations of the triggers otherwise discussed herein. For example, timing information may be predefined within the aerosol delivery device to identify a specific length, number, and/or sequence of detected flows of air to implement a predefined trigger.

In some example implementations in which the control body 102 includes the control component 208 and the communication interface 246, the control body may be coupleable to a charging component and the cartridge 104. In these example implementations, the trigger may further include coupling of the control body to the charging component or cartridge. And in at least some of these example implementations, the at least one instance in which the flow of air is detected is the first instance in which the flow of air is detected after the coupling of the control body to the cartridge. As such, broadcasting availability may occur any time after the user connects and/or couples the control body to either a cartridge or charging component, and takes at least one puff.

In some example implementations, detection of the coupling of the control body 102 to either the cartridge 104 or charging component results in an enablement within software of the control body. In at least some of these example implementations, this software may then cause broadcasting availability to occur on the next single puff only such that if another initiation of broadcasting availability is required, the control body must first disconnect from the cartridge or control component. The subsequent initiation of broadcasting availability may then occur after a recoupling of the control body, and thereafter another initial single puff.

In some example implementations in which the communication interface 246 may be or include a Bluetooth communication interface, broadcasting availability may include the Bluetooth communication interface being caused to transmit an advertisement that includes information for connecting the Bluetooth communication interface with a capable Bluetooth-enabled device. As used herein, the transmission of an advertisement that includes information for connecting the Bluetooth communication interface with a capable Bluetooth-enabled device may be referred to as "advertising availability" or even more simply "advertising". In at least one instance, the Bluetooth communication interface may bond with the capable Bluetooth-enabled device upon connection.

It should be noted that although many of the example implementations discussed herein specifically reference Bluetooth communication technologies (e.g., Bluetooth Low Energy), the example implementations may be used in conjunction with other wireless communication technologies not explicitly stated herein including near field communication (NFC) technologies, wireless personal area network (WPAN) technologies ZigBee, infrared (e.g., IrDA), radio-frequency identification (RFID), Wireless USB, Wi-Fi (e.g., Wi-Fi direct) and the like. As such, implementations in which the communication interface 246 may be or include a Bluetooth communication interface only represent one example implementation of the present disclosure.

In some example implementations, the Bluetooth communication interface being caused to transmit the advertisement includes being caused to transmit the advertisement for a length of time no longer than a predetermined length of time after the first instance in which the flow of air detected, and thereafter cease transmission of the advertisement. For example, the Bluetooth communication interface may initialize advertising availability for 30 seconds after the first instance in which the flow of air detected, and thereafter cease advertising availability.

Figure 3:
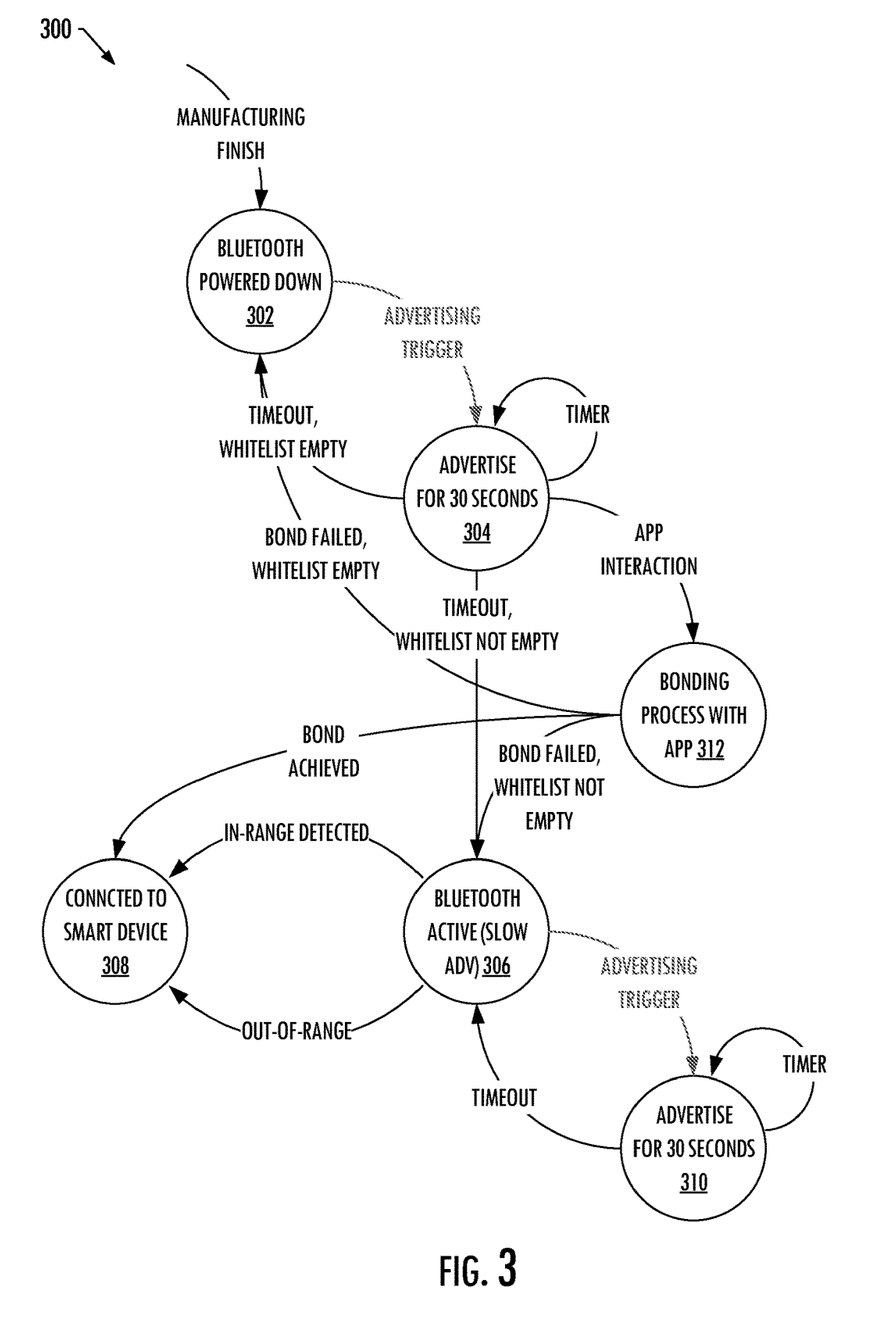

FIG. 3 illustrates a state diagram 300 for trigger-based Bluetooth advertising, according to an example implementation of the present disclosure. In some example implementations in which the communication interface 246 may be or include a Bluetooth communication interface, the Bluetooth communication interface may be set in an initial state 302 during the process of manufacturing the aerosol delivery device 100. In this initial state, the Bluetooth communication interface, and more particularly a power source of the Bluetooth communication interface, may be disabled until an initial detection of at least one trigger.

After the detection of the at least one trigger, the Bluetooth communication interface may enter an initial advertising state 304 in which the Bluetooth communication interface may advertise for a predetermined duration (e.g., 30 seconds). In one example, the advertising state may be associated with a timer that is set based at least in part on the predetermined duration. In another example, expiration of the timer may initialize a timeout period.

The Bluetooth communication interface may include a whitelist that specifies one or more identifiers of any Bluetooth-enabled devices with which the Bluetooth communication interface has previously bonded and/or is allowed to bond (e.g., trusted Bluetooth-enabled devices). In one example implementation, if the timer has expired thereby initiating the timeout period during the initial advertising state 304, and the whitelist is empty, the Bluetooth communication interface may re-enter the initial state 302. Alternatively, if the timer has expired thereby initiating the timeout period and the whitelist is not empty (e.g., the whitelist has one or more entries), the Bluetooth communication interface may enter an active state 306 during which the Bluetooth communication interface may be configured to slow advertise if not actively connected to an in-range Bluetooth-enabled device.

During the active state 306, the Bluetooth communication interface may detect and connect with an in-range Bluetooth-enabled device, and thereby enter a connected state 308. In an instance in which the connected device becomes out-of-range, the Bluetooth communication interface may re-enter the active state. Also during the active state, a trigger may be detected at the aerosol delivery device 100 causing the Bluetooth communication interface to enter a secondary advertising state 310. In this state, the Bluetooth communication interface may advertise for a predetermined duration such as 30 seconds, or otherwise advertise until the expiration of the timer in which the timeout period may initialize and the Bluetooth communication interface may re-enter the active state.

Referring again to the initial advertising state 304, if the Bluetooth communication interface receives a response from a capable Bluetooth-enable device, the Bluetooth communication interface may initiate a bonding process 312 with the Bluetooth-enabled device. In one example implementation, if the bonding process fails, and the whitelist is empty, the Bluetooth communication interface may re-enter the initial state 302. Alternatively, if the bonding process fails (or is successful), and the whitelist is not empty, the Bluetooth communication interface may enter the active state 306. Otherwise, if the bonding process is successful, the Bluetooth communication interface may connect with the responsive Bluetooth-enabled device and thereby enter the connected state 308.

In some example implementations, in an instance in which the white list is not empty, the Bluetooth communication interface may determine the subsequent state following the bonding process 312 based at least in part on whether or not the previously bonded Bluetooth-enabled device is in range. In one implementation, for example, if a previously or recently bonded Bluetooth-enabled device is in range the Bluetooth communication interface may enter the connected state 308. If a previously bonded Bluetooth-enabled device (i.e., the white list is not empty) is not in range the Bluetooth communication interface may enter the active state 306.

Figure 4:
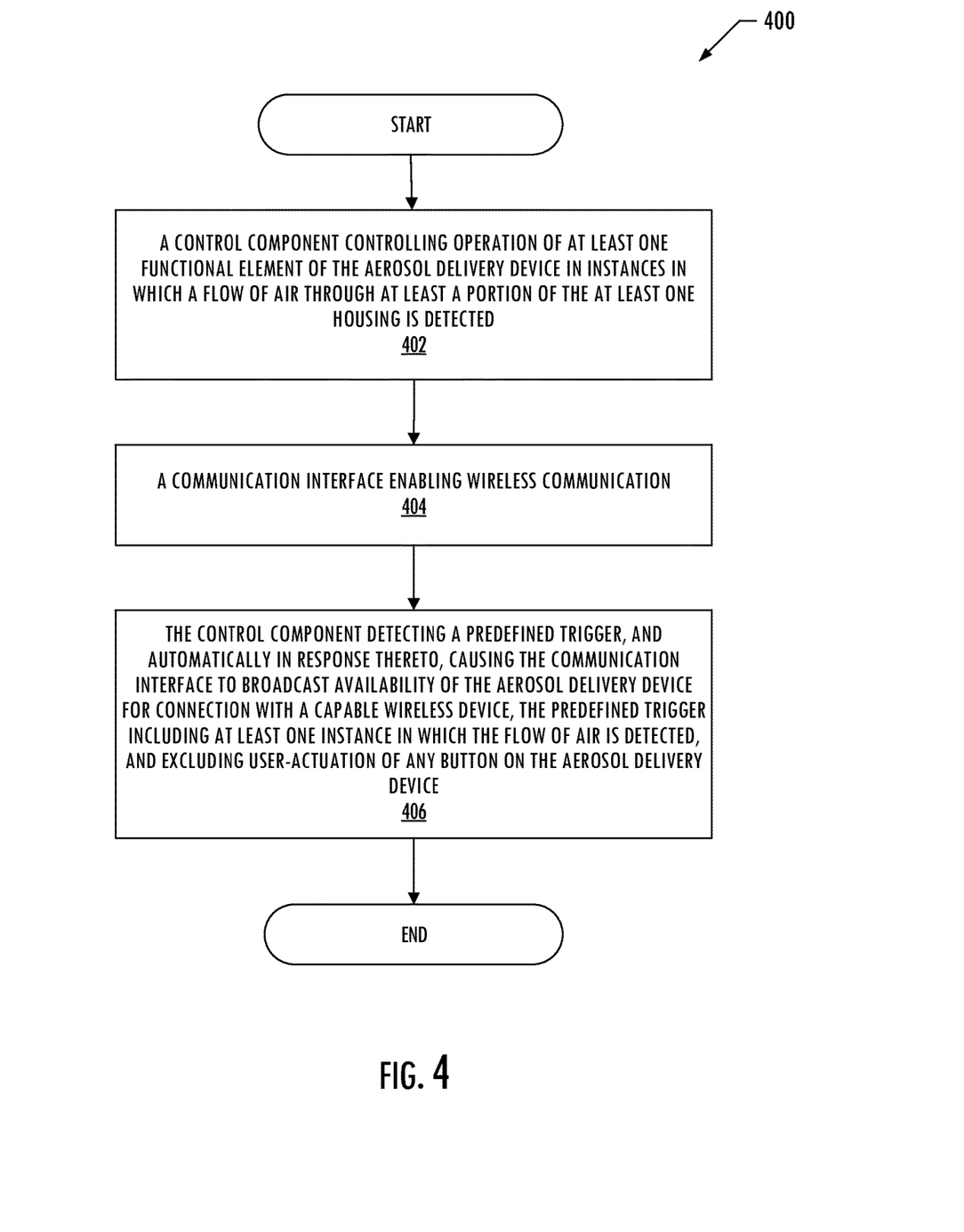

FIG. 4 illustrates various operations in a method 400 of operation of an aerosol delivery device. As shown at block 402, the method may include a control component controlling operation of at least one functional element of the aerosol delivery device in instances in which a flow of air through at least a portion of the at least one housing is detected. As shown at block 404, the method may also include a communication interface enabling wireless communication. As shown at block 406, the method may also include the control component further detecting a predefined trigger, and automatically in response thereto, causing the communication interface to broadcast availability of the aerosol delivery device for connection with a capable wireless device. The predefined trigger includes at least one instance in which the flow of air is detected, and excludes user-actuation of any button on the aerosol delivery device.

Figure 1:
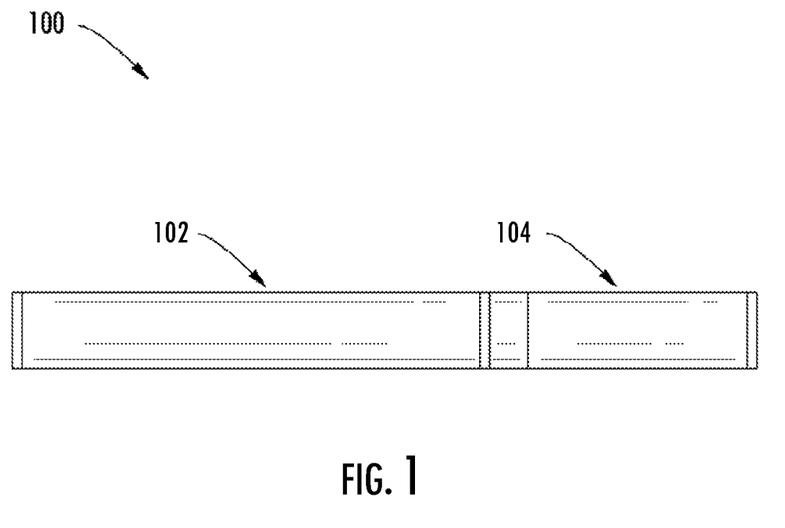
FIG. 1 illustrates a side view of an aerosol delivery device including a cartridge coupled to a control body, according to an example implementation of the present disclosure.

The foregoing description of use of the article(s) can be applied to the various example implementations described herein through minor modifications, which can be apparent to the person of skill in the art in light of the further disclosure provided herein. The above description of use, however, is not intended to limit the use of the article but is provided to comply with all necessary requirements of disclosure of the present disclosure. Any of the elements shown in the article(s) illustrated in FIGS. 1-3 or as otherwise described above may be included in an aerosol delivery device according to the present disclosure.

Many modifications and other implementations of the disclosure set forth herein will come to mind to one skilled in the art to which these disclosure pertain having the benefit of the teachings presented in the foregoing descriptions and the associated drawings. Therefore, it is to be understood that the disclosure are not to be limited to the specific implementations disclosed and that modifications and other implementations are intended to be included within the scope of the appended claims. Moreover, although the foregoing descriptions and the associated drawings describe example implementations in the context of certain example combinations of elements and/or functions, it should be appreciated that different combinations of elements and/or functions may be provided by alternative implementations without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. A method of operation of an aerosol delivery device comprising a control body coupleable to a cartridge, the method comprising at the aerosol delivery device:
   a control component controlling operation of at least one functional element of the aerosol delivery device in instances in which a flow of air through at least a portion of at least one housing is detected;
   a communication interface enabling wireless communication; and
   the control component further detecting at least one predefined trigger, and automatically in response thereto, causing the communication interface to broadcast availability of the aerosol delivery device for connection with a capable wireless device, a predefined trigger of the at least one predefined trigger including coupling of the control body to the cartridge, and a first instance in which the flow of air is detected after the control body is coupled to the cartridge, and excluding user-actuation of any button on the aerosol delivery device, and wherein the control component is configured to cause the communication interface to broadcast availability in response to detection of a subsequent instance of the predefined trigger only after the control body is decoupled from the cartridge and recoupled to the cartridge or another cartridge.

2. The method of claim 1, wherein another predefined trigger of the at least one predefined trigger includes a predefined length of time between at least two instances in which the flow of air is detected.

3. The method of claim 2, wherein the predefined length of time is no more than 1,250 milliseconds between the at least two instances in which the flow of air is detected.

4. The method of claim 1, wherein the predefined trigger includes the first instance in which the flow of air is detected for a predefined duration after the control body is coupled to the cartridge.

5. The method of claim 4, wherein the predefined duration is between 70 and 750 milliseconds.

6. The method of claim 1, wherein another predefined trigger of the at least one predefined trigger includes a predefined number of instances in which the flow of air is detected.

7. The method of claim 1, wherein the control body is also coupleable to a charging component, and wherein another predefined trigger of the at least one predefined trigger includes coupling of the control body to the charging component.

8. The method of claim 1, wherein the communication interface is a Bluetooth communication interface, and wherein the communication interface broadcasting availability includes the Bluetooth communication interface transmitting an advertisement that includes information for connecting the Bluetooth communication interface with a capable Bluetooth-enabled device, and in at least one instance, bonding with the capable Bluetooth-enabled device upon connection.

9. The method of claim 8, wherein the Bluetooth communication interface transmitting the advertisement includes transmitting the advertisement for a length of time no longer than a predetermined length of time after the first instance in which the flow of air is detected after the control body is coupled to the cartridge, and thereafter cease transmission of the advertisement.

10. An aerosol delivery device comprising a control body coupleable to a cartridge, the control body comprising:

at least one housing; and contained within the at least one housing, a control component configured to control operation of at least one functional element of the aerosol delivery device in instances in which a flow of air through at least a portion of the at least one housing is detected; and a communication interface coupled to the control component and configured to enable wireless communication, wherein the control component is further configured to detect at least one predefined trigger, and automatically in response thereto, cause the communication interface to broadcast availability of the aerosol delivery device for connection with a capable wireless device, a predefined trigger of the at least one predefined trigger including coupling of the control body to the cartridge, and a first instance in which the flow of air is detected after the control body is coupled to the cartridge, and excluding user-actuation of any button on the aerosol delivery device, and wherein the control component is configured to cause the communication interface to broadcast availability in response to detection of a subsequent instance of the predefined trigger only after the control body is decoupled from the cartridge and recoupled to the cartridge or another cartridge.

11. The aerosol delivery device of claim 10, wherein another predefined trigger of the at least one predefined trigger includes a predefined length of time between at least two instances in which the flow of air is detected.

12. The aerosol delivery device of claim 11, wherein the predefined length of time is no more than 1,250 milliseconds between the at least two instances in which the flow of air is detected.

13. The aerosol delivery device of claim 10, wherein the predefined trigger includes the first instance in which the flow of air is detected for a predefined duration after the control body is coupled to the cartridge.

14. The aerosol delivery device of claim 13, wherein the predefined duration is between 70 and 750 milliseconds.

15. The aerosol delivery device of claim 10, wherein another predefined trigger of the at least one predefined trigger includes a predefined number of instances in which the flow of air is detected.

16. The aerosol delivery device of claim 10, wherein the control body is also coupleable to a charging component, and wherein another predefined trigger of the at least one predefined trigger includes coupling of the control body to the charging component.

17. The aerosol delivery device of claim 10, wherein the communication interface is a Bluetooth communication interface, and wherein the communication interface being caused to broadcast availability includes the Bluetooth communication interface being caused to transmit an advertisement that includes information for connecting the Bluetooth communication interface with a capable Bluetooth-enabled device, and in at least one instance, bond with the capable Bluetooth-enabled device upon connection.

18. The aerosol delivery device of claim 17, wherein the Bluetooth communication interface being caused to transmit the advertisement includes being caused to transmit the advertisement for a length of time no longer than a predetermined length of time after the first instance in which the flow of air is detected after the control body is coupled to the cartridge, and thereafter cease transmission of the advertisement.

* * * * *